United States Patent [19]

Rupilius et al.

[11] Patent Number: 4,747,969
[45] Date of Patent: May 31, 1988

[54] PROCESS FOR THE PRODUCTION OF FATTY ACID MIXTURES CONTAINING A HIGH PROPORTION OF $C_6$–$C_{10}$-FATTY ACIDS

[75] Inventors: Wolfgang Rupilius; Karl Hentschel, both of Düsseldorf, Fed. Rep. of Germany

[73] Assignee: Henkel Kommanditgesellschaft auf Aktien, Duesseldorf, Fed. Rep. of Germany

[21] Appl. No.: 14,098

[22] Filed: Jan. 29, 1987

Related U.S. Application Data

[63] Continuation of Ser. No. 694,902, Jan. 25, 1985, abandoned.

[30] Foreign Application Priority Data

Jan. 28, 1984 [DE] Fed. Rep. of Germany ....... 3403021

[51] Int. Cl.$^4$ .......................... C11C 3/02; C11C 1/04
[52] U.S. Cl. .................................. 260/415; 260/410.7
[58] Field of Search .............................. 260/410.7, 415

[56] References Cited

U.S. PATENT DOCUMENTS 3,551,464 12/1970 Miller et al. ..................... 260/410.6

FOREIGN PATENT DOCUMENTS 1206623 8/1959 France .
0808634 2/1959 United Kingdom .

OTHER PUBLICATIONS

Smirnov; A. P., *Chemical Abstracts* 69:37339t, (1968).
Wagner & Zook, *Synthetic Organic Chemistry*, pp. 486–487, 1953.
Pattison, *Fatty Acids and Their Industrial Applications*, pp. 25–29, 1968.

*Primary Examiner*—Charles F. Warren
*Assistant Examiner*—Elizabeth A. Hanley
*Attorney, Agent, or Firm*—Ernest G. Szoke; Henry E. Millson, Jr.

[57] ABSTRACT

A process for the production of fatty acid mixtures containing a high proportion of $C_6$–$C_{10}$-fatty acids consisting essentially of (1) transesterifying mixtures consisting essentially of $C_6$–$C_{10}$-fatty acid alkyl esters with from 1 to 4 carbon atoms in the alkyl with glycerine at 160° to 250° C. in the presence of transesterification catalysts with removal of the $C_1$–$C_4$-alkanol formed, (2) adding the $C_6$–$C_{10}$-fatty acid glycerides to a $C_6$–$C_{18}$-fatty acid glyceride selected from the group consisting of coconut oil, palm kernel oil and mixtures thereof, (3) subjecting the mixture of glycerides to lipolysis in the presence of an excess of water at 200° C. to 250° C. at the autogenous pressure in the absence of a catalyst until until the required degree of splitting is achieved and (4) recovering a fatty acid mixture containing a high proportion of $C_6$–$C_{10}$-fatty acids.

3 Claims, No Drawings

PROCESS FOR THE PRODUCTION OF FATTY ACID MIXTURES CONTAINING A HIGH PROPORTION OF $C_6$–$C_{10}$-FATTY ACIDS

This application is a continuation, of application Ser. No. 694,902, filed Jan. 25, 1985, now abandoned.

BACKGROUND OF THE INVENTION

The present invention relates to a process for the production of fatty acid mixtures containing a high proportion of $C_6$–$C_{10}$-fatty acids.

Esters of naturally occurring fatty acids and short-chain aliphatic alcohols, particularly fatty acid methyl esters, are of considerable commercial significance, above all as starting materials for the production of fatty alcohols and derivatives thereof. However, they are also used for the production of other oleochemical products, for example fatty acid alkanolamides, fatty acid ester sulfonates and soaps. In view of the performance properties required of the end products, alkyl esters of fatty acids containing from 12 to 18 carbon atoms, particularly in the form of mixtures, are of particular interest for the abovementioned applications. Fatty acid ester mixtures such as these are primarily obtained by the catalytic transesterification of fats and oils of natural origin, which are known to consist of fatty acid triglycerides, with the corresponding short-chain alcohols, above all with methanol.

When subjected to direct catalytic transesterification, most naturally occurring fats and oils give ester mixtures of which the fatty acid component consists of $C_{12}$–$C_{18}$-fatty acids. If coconut oil or palm kernel oil is used as starting material for transesterification, the ester mixtures obtained contain a high percentage of esters of short-chain fatty acids, the presence of which is generally undesirable. For this reason, the alkyl ester mixtures obtained from coconut oil and palm kernel oil by transesterification are generally separated by distillation into a low-boiling fraction, which contains the alkyl esters of the $C_6$–$C_{10}$-fatty acids (first runnings fatty acid alkyl esters), and a higher-boiling fraction which contains the alkyl esters of the $C_{12}$–$C_{18}$-fatty acids.

The main fraction of the coconut oil and palm kernel oil fatty acid alkyl esters serves as starting material for the production of fatty alcohols and fatty acid alkanolamides. Part of the first runnings fatty acid alkyl esters separated off is processed by highpressure hydrogenation into $C_6$–$C_{10}$-fatty alcohols. The remainder is split by hydrolysis into the free $C_6$–$C_{10}$-fatty acids which are then marketed as first runnings fatty acids, also known as feed fatty acids.

The first runnings fatty acid alkyl esters may be converted into the free fatty acids in known manner by alkaline hydrolysis and subsequent decomposition of the soaps with mineral acids or by acid hydrolysis in the presence of acidic catalysts.

Alkaline hydrolysis involves considerable outlay on chemicals because stoichiometric quantities of alkali metal hydroxide and mineral acids have to be used. In addition, the aqueous alkali metal salt solutions formed give rise to considerable effluent pollution.

The acid-catalyzed hydrolysis of the $C_6$–$C_{10}$-fatty acid alkyl esters is an equilibrium reaction which can only be continued to a satisfactory conversion level when water is used in a large excess. In this connection, particular problems are caused by the fact that the esters to be reacted dissolve very readily in the free fatty acids formed so that the velocity of the hydrolysis reaction is seriously reduced. Under practical conditions, satisfactory $C_6$–$C_{10}$-fatty acids can only be obtained when the fractions of alkyl esters still present at the end of hydrolysis are removed with steam. Also, aqueous alcohol solutions which have to be worked up by fractional distillation are again formed just as in the alkaline hydrolysis of the $C_6$–$C_{10}$-fatty acid esters.

OBJECTS OF THE INVENTION

An object of the present invention is to provide a process by means of which the free $C_6$–$C_{10}$-fatty acids may readily be obtained from the first runnings fatty acid esters of short-chain alcohols without any of the disadvantages of the known processes.

Another object of the present invention is the development of a process for the production of fatty acid mixtures containing a high proportion of $C_6$–$C_{10}$-fatty acids consisting essentially of 1) transesterifying mixtures consisting essentially of $C_6$–$C_{10}$-fatty acid alkyl esters with from 1 to 4 carbon atoms in the alkyl with glycerine at 160° to 250° C. in the presence of transesterification catalysts with removal of the $C_1$–$C_4$-alkanol formed, 2) adding the $C_6$–$C_{10}$-fatty acid glycerides to a $C_6$–$C_{18}$-fatty acid glyceride selected from the groups consisting of coconut oil, palm kernel oil and mixtures thereof, 3) subjecting the mixture of glycerides to lipolysis in the presence of an excess of water at 200° to 250° C. at the autogenous pressure in the absence of a catalyst until the required degree of splitting is achieved and 4) recovering a fatty acid mixture containing a high proportion of $C_6$–$C_{10}$-fatty acids.

A further object of the present invention is the development of an improvement in the process for the production of fatty acid mixtures from fatty acid glycerides by subjecting a mixture of fatty acid glycerides to lipolysis in the presence of an excess of water at 200° to 250° C. at the autogenous pressure in the absence of a catalyst until the required degree of splitting is achieved and recovering a fatty acid mixture, the improvement consisting of utilizing a mixture of $C_6$–$C_{10}$-fatty acid glycerides and $C_6$–$C_{18}$-fatty acid glycerides selected from the group consisting of coconut oil, palm kernel oil and mixtures thereof in a ratio by weight of from 1:19 to 1:3, and recovering a fatty acid mixture in at least 15% less time than that required to lipolyze said $C_6$–$C_{18}$-fatty acid glycerides selected from the group consisting of coconut oil, palm kernel oil and mixtures thereof under the same conditions.

These and other objects of the invention will become more apparent as the description thereof proceeds.

DESCRIPTION OF THE INVENTION

The above objects are achieved in that the first runnings fatty acid esters of short-chain alcohols are readily transesterified with glycerine in the presence of alkaline catalysts to form the corresponding glycerides and that these $C_6$–$C_{10}$-fatty acid glycerides may be hydrolyzed in admixture with natural fats and oils, particularly coconut oil and palm kernel oil, under lipolysis conditions to form fatty acid mixtures which contain a high percentage of $C_6$–$C_{10}$-fatty acids and from which the C6-C10-fatty acids may readily be recovered by distillation.

Accordingly, the present invention relates to a process for the production of fatty acid mixtures containing a high proportion of $C_6$–$C_{10}$-fatty acids by the hydrolysis of fatty acid glycerides, characterized in that mixtures consisting essentially of $C_6$–$C_{10}$-fatty acid alkyl esters with from 1 to 4 carbon atoms in the alkyl are transesterified with glycerine in the presence of esterification catalysts at 160° to 250° C., the glycerides obtained are subjected to lipolysis known per se in admixture with coconut oil and/or palm kernel oil and the fatty acids released can be isolated.

More particularly, the present invention relates to a process for the production of fatty acid mixtures containing a high proportion of $C_6$–$C_{10}$-fatty acids consisting essentially of 1) transesterifying mixtures consisting essentially of $C_6$–$C_{10}$-fatty acid alkyl esters with from 1 to 4 carbon atoms in the alkyl with glycerine at 160° to 250° C. in the presence of transesterification catalysts with removal of the $C_1$–$C_4$-alkanol formed, 2) adding the $C_6$–$C_{10}$-fatty acid glycerides to a $C_6$–$C_{18}$-fatty acid glyceride selected from the groups consisting of coconut oil, palm kernel oil and mixtures thereof, 3) subjecting the mixture of glycerides to lipolysis in the presence of an excess of water at 200° to 250° C. at the autogenous pressure in the absence of a catalyst until the required degree of splitting is achieved and 4) recovering a fatty acid mixture containing a high proportion of $C_6$–$C_{10}$-fatty acids.

As mentioned above, the mixtures of first runnings fatty acid alkyl esters containing from 1 to 4 carbon atoms used as starting material in accordance with the invention are obtained as secondary product in the production of fatty alcohols from coconut oil or palm kernel oil. The acid component of these alkyl esters consists of caprylic, caproic and capric acid. Small quantities of lauric acid may also be present. The quantitative ratios in which the $C_6$–$C_{10}$-fatty acids occur in the first runnings fatty acid ester mixtures are subject to variations within a wide range depending on the origin of the native raw materials and on the process used for separation by distillation. The following are typical examples of the composition of the acid component of first runnings fatty acid alkyl esters used as starting material in accordance with the invention:

First runnings fatty acid alkyl ester cut from coconut oil

| Caproic acid | traces |
|---|---|
| Caprylic acid | 88.5% by weight |
| Capric acid | 11.5% by weight |

First runnings fatty acid alkyl ester from palm kernel oil

| Caproic acid | 1.2% by weight |
|---|---|
| Caprylic acid | 59.7% by weight |
| Capric acid | 34.6% by weight |
| Lauric acid | 4.5% by weight |

The alcohol component of the first runnings fatty acid alkyl esters may be ethanol, n-propanol, isopropanol, n-butanol, sec.-butanol, tert.-butanol and, preferably, methanol.

Technical glycerine may be used for the transesterification reaction. Crude glycerine derived from lipolysis is preferably used. The water present therein is best distilled off by heating in vacuo to 140°–160° C. before the first runnings fatty acid alkyl ester and the catalyst are added.

Where transesterification is carried out with glycerine, it is best for the molar ratio of first runnings fatty acid alkyl ester to glycerine to be no less than 1:1. The first runnings fatty acid alkyl esters are preferably transesterified with glycerine in a molar ratio of from 2:1 to 3:1.

Suitable catalysts for the transesterification with glycerine are virtually any esterification catalysts, for example acidic catalysts, such as hydrogen chloride, sulfuric acid, phosphoric acid, boron trifluoride, aluminium chloride, trichloroacetic acid, alkyl sulfuric acids and organic sulfonic acids or alkaline esterification catalysts, such as alkali metal hydroxides, carbonates and acetates, alkaline-earth metal oxides, hydroxides, carbonates and acetates and also alkali metal and alkaline-earth metal salts of fatty acids containing from 6 to 22 carbon atoms. Titanium compounds, such as organic titanates, metallic tin and organotin compounds, such as mono- and dialkyl tin derivatives, are also suitable transesterification catalysts. The transesterification reaction is preferably carried out with alkaline catalysts, particularly sodium hydroxide. The catalysts are added to the reaction mixture in quantities of from 0.05% to 1% by weight, based on the quantity of first runnings fatty acid alkyl ester used.

Transesterification takes place smoothly at temperatures of from 160° to 250° C. under normal, pressure. In the practical application of the process according to the invention, the reaction mixture is rapidly heated to the temperature at which the beginning of the reaction is reflected in the distilling over of the monoalcohol released. Thereafter, the temperature of the reaction mixture is only increased at the rate required for the uniform removal by distillation of the monoalcohol formed. It has been found to be advisable briefly to apply a vacuum (approx. 15–40 mbar) at the end of the reaction in order to remove any traces of first runnings fatty acid alkyl esters which may still be present from the reaction mixture. The transesterification products obtained in this way may immediately pass onto the next stage of the process.

To carry out splitting of the fatty acids, the $C_6$–$C_{10}$-fatty acid glycerides obtained are mixed with coconut oil and/or palm kernel oil. It has been found to be advisable to use these materials in a ratio by weight of from 1:19 to 1:3. The mixtures of native oils and $C_6$–$C_{10}$-fatty acid glycerides are then heated with from 100% to 300% by weight of water and preferably with from 150% to 250% by weight of water, based on the total quantity of fatty acid glycerides to be reacted, to 200°–250° C. in the absence of a catalyst in a closed reactor under the autogenous pressure spontaneously established and kept at that temperature until the required degree of splitting is reached. It has surprisingly been found that the splitting of coconut oil and palm kernel oil is considerably accelerated by the addition of $C_6$–$C_{10}$-fatty acid glycerides. For example, it has been found that, with pure coconut oil at 225° C., the splitting equilibrium with approx. 95% of free fatty acids is only reached after 240 minutes. If a mixture of 90 parts by weight of coconut oil and 10 parts by weight of first runnings fatty acid glyceride is used, the splitting equilibrium is reached after only 180 minutes.

The present invention therefore also relates to an improvement in the process for the production of fatty acid mixtures from fatty acid glycerides by subjecting a mixture of fatty acid glycerides to lipolysis in the presence of an excess of water at 200° to 250° C. at the autogenous pressure in the absence of a catalyst until the required degree of splitting is achieved and recovering a fatty acid mixture, the improvement consisting of utilizing a mixture of $C_6$-$C_{10}$-fatty acid glycerides and $C_6$-$C_{18}$-fatty acid glycerides selected from the group consisting of coconut oil, palm kernel oil and mixtures thereof in a ratio by weight of from 1:19 to 1:3, and recovering a fatty acid mixture in at least 15% less time than that required to lipolyze said $C_6$-$C_{18}$-fatty acid glycerides selected from the group consisting of coconut oil, palm kernel oil and mixtures thereof under the same conditions.

The fatty acids liberated may readily be separated off as organic phase from the reaction mixture obtained during the pressure splitting process and subsequently purified by washing.

In the fatty acids obtained in this way, the $C_6$-$C_{10}$-fatty acids are enriched to a more or less considerable extent, depending on the preceding addition of $C_6$-$C_{10}$-fatty acid glycerides. In general, the mixing ratios in the fatty acid splitting of mixtures of $C_6$-$C_{10}$-fatty acid glycerides and coconut oil or palm kernel oil will be selected in such a way that the fatty acid mixtures formed contain from 10% to 40% by weight of $C_6$-$C_{10}$-fatty acids and, more specifically, from 0 to 10% by weight of caproic acid, from 5% to 35% by weight of caprylic acid and from 5% to 35% by weight of capric acid.

The feed fatty acids may readily be separated off by vacuum distillation from the fatty acid mixtures obtained with a high content of $C_6$-$C_{10}$-fatty acids. The feed fatty acid fractions obtained in this way are used primarily as starting material for the production of ester lubricants.

The following specific embodiments are illustrative of the practice of the invention without being limitative thereto.

EXAMPLE (A) Reaction with glycerine

The starting material used was a feed fraction containing approx. 88.5% by weight of caprylic acid methyl ester, 11.5% by weight of capric acid methyl ester and traces of caproic acid methyl ester which had been separated off by distillation from a coconut oil fatty acid methyl ester mixture. The starting material had an acid number of 0.2 and a saponification number of 348.

In a stirrer-equipped vessel with a fractionating column, 1.44 kg of crude glycerine (12.5 mols) from lipolysis (approx. 80% by weight of glycerine) were dehydrated with stirring and heating to 150° C. under a water jet vacuum. 4.83 kg (30 mols) of starting material and 10 g of sodium hydroxide (50% by weight solution; 0.1% by weight of NaOH, based on fatty acid methyl ester) were then added. The temperature of the mixtures was then slowly increased with stirring under normal pressure. At 160° C., the onset of the transesterification reaction was reflected in the distilling over of methanol. The temperature of the mixture was increased to 220° C. over a period of 4 hours. Finally, a vacuum (approx. 20 mbar) was briefly applied to remove traces of unreacted methyl ester. Distillation was terminated when fatty acid monoglyceride appeared in the distillate (recognizable from the higher viscosity).

The $C_6$-$C_{10}$-fatty acid glyceride mixture obtained had an acid number of 0.6 and a saponification number of 304.9.

(B) Lipolysis (1) In a 5-liter-capacity stirrer-equipped autoclave, 2 kg of water were heated to 225° C. before 1 kg of a mixture of 95% by weight of coconut oil (composition of the fatty acid component in percent by weight: 0.7 $C_6$; 8.0 $C_8$; 6.2 $C_{10}$; 48.1 $C_{12}$; 17.6 $C_{14}$; 8.6 $C_{16}$; 10.8 $C_{18}$; acid number 5.6; saponification number 254.6) and 5% by weight of the above-described $C_6$-$C_{10}$-fatty acid glyceride was introduced into the autoclave by a feed pump. The mixture formed was kept at a temperature of 225° C. while at the same time, samples for determining the prevailing acid numbers and saponification numbers were removed at regular intervals through a valve. It was found from the analytical data that a degree of splitting of 95% was reached after 200 minutes.

According to analysis by gas chromatography, the fatty acid mixture isolated from the reaction mixture had the following composition (in % by weight): 0.6 $C_6$; 11.9 $C_8$; 6.6 $C_{10}$; 45.9 $C_{12}$; 16.5 $C_{14}$; 8.3 $C_{16}$; 10.2 $C_{18}$.

(2) As in B1, a mixture of 90% by weight of coconut oil and 10% by weight of the above described $C_6$-$C_{10}$-fatty acid glyceride was subjected to lipolysis at 225° C. A degree of splitting of 95% was reached after 65 minutes.

According to analysis by gas chromatography, the fatty acid mixture obtained from the reaction mixture had the following composition (in % by weight): 0.6 $C_6$; 6.2 $C_8$; 6.7 $C_{10}$; 43.5 $C_{12}$; 15.6 $C_{14}$; 7.7 $C_{16}$; 9.7 $C_{18}$.

(3) As in B1, a mixture of 75% by weight of coconut oil and 25% by weight of the above described $C_6$-$C_{10}$-fatty acid glyceride was subjected to lipolysis at 25° C. A degree of splitting of 95% was obtained after 40 minutes.

According to analysis by gas chromatography, the fatty acid mixture obtained from the reaction mixture had the following composition (in % by weight): 0.4 $C_6$; 28.1 $C_8$; 7.7 $C_{10}$; 36.2 $C_{12}$; 13.2 $C_{14}$; 6.3 $C_{16}$; 8.1 $C_{18}$.

(4) For comparison purposes, coconut oil was subjected to lipolysis under the same conditions as in B1, but without any addition of the above described $C_6$-$C_{10}$-fatty acid glyceride. A degree of splitting of 95% was only obtained after 240 minutes.

The preceding specific embodiments are illustrative of the practice of the invention. It is to be understood however that other expedients known to those skilled in the art or disclosed herein may be employed without departing from the spirit of the invention or the scope of the appended claims.

We claim:

1. A process for the production of fatty acid mixtures containing a high proportion of $C_6$-$C_{10}$-fatty acids consisting essentially of (1) transesterifying mixtures consisting essentially of $C_6$-$C_{10}$-fatty acid alkyl esters with from 1 to 4 carbon atoms in the alkyl with glycerine, wherein the molar ratio of $C_6$-$C_{10}$-fatty acid alkyl esters to glycerine is from 2:1 to 3:1, at 160° to 250° C. in the presence of an alkaline transesterification catlayst with removal of the $C_1$-$C_4$-alkanol formed, (2) adding the resulting C6-C10-fatty acid glycerides to a naturally occurring glyceride selected from the group consisting of coconut oil, palm kernel oil and mixtures thereof, in a weight ratio of $C_6$-$C_{10}$-fatty acid glyceride to naturally occurring glyceride of from 1:19 to 1:3, (3) subjecting the mixture of glycerides to lipolysis in the presence of an excess of water at 200° to 250° C. at the autogenous pressure in the absence of a catalyst until splitting equilibrium is achieved and (4) recovering a fatty acid mixture containing a high proportion of $C_6$–$C_{10}$-fatty acids.

2. The process of claim 1 wherein said $C_6$–$C_{10}$-fatty acid alkyl ester is the methyl ester.

3. An improvement in the process for the production of fatty acid mixtures from fatty acid glycerides by subjecting a mixture of fatty acid glycerides to lipolysis in the presence of an excess of water at 200° to 250° C. at the autogenous pressure in the absence of a catalyst until splitting equilibrium is achieved and recovering a fatty acid mixture, the improvement consisting of utilizing a mixture of $C_6$–$C_{10}$-fatty acid glycerides and glycerides selected from the group consisting of coconut oil, palm kernel oil and mixtures thereof in a ratio by weight of from 1:19 to 1:3, and recovering a fatty acid mixture in at least 15% less time than that required to lipolyze said glycerides selected from the group consisting of coconut oil, palm kernel oil and mixtures thereof under the same conditions.

* * * * *